United States Patent
Van Epps et al.

(10) Patent No.: US 8,506,627 B2
(45) Date of Patent: Aug. 13, 2013

(54) SOFT FILLED PROSTHESIS SHELL WITH DISCRETE FIXATION SURFACES

(75) Inventors: Dennis Van Epps, Goleta, CA (US); Thomas E. Powell, Santa Barbara, CA (US)

(73) Assignee: Allergan, Inc., Irvine, CA (US)

( * ) Notice: Subject to any disclaimer, the term of this patent is extended or adjusted under 35 U.S.C. 154(b) by 233 days.

(21) Appl. No.: 12/540,317

(22) Filed: Aug. 12, 2009

(65) Prior Publication Data
US 2010/0042212 A1   Feb. 18, 2010

Related U.S. Application Data

(60) Provisional application No. 61/088,418, filed on Aug. 13, 2008.

(51) Int. Cl.
*A61F 2/12* (2006.01)
(52) U.S. Cl.
USPC .............................................. 623/8
(58) Field of Classification Search
USPC ............................................ 623/7–8
See application file for complete search history.

(56) References Cited

U.S. PATENT DOCUMENTS

| | | |
|---|---|---|
| 2,805,208 A | 9/1957 | Roche |
| 3,189,921 A | 6/1965 | Pangman |
| 3,293,663 A | 12/1966 | Cronin |
| 3,366,975 A | 2/1968 | Pangman |
| 3,559,214 A | 2/1971 | Pangman |
| 3,600,718 A | 8/1971 | Boone |
| 3,665,520 A | 5/1972 | Perras |
| 3,700,380 A | 10/1972 | Kitrilakis |
| 3,852,832 A | 12/1974 | McGhan |
| 3,934,274 A | 1/1976 | Hartley |
| 4,034,751 A | 7/1977 | Hung |
| 4,157,085 A | 6/1979 | Austad |
| 4,231,979 A | 11/1980 | White |
| 4,264,990 A | 5/1981 | Hamas |
| 4,298,997 A | 11/1981 | Rybka |
| 4,298,998 A | 11/1981 | Naficy |

(Continued)

FOREIGN PATENT DOCUMENTS

| | | |
|---|---|---|
| EP | 0230672 A2 | 8/1987 |
| EP | 0315814 | 5/1989 |

(Continued)

OTHER PUBLICATIONS

Antonius Mikes et al, 2000, Formation of Highly Porous Biodegradable Scaffolds for Tissue Engineering, Electronic Journal of Biotechnology, 3(2), 114-119.

(Continued)

*Primary Examiner* — Suzette J Gherbi
(74) *Attorney, Agent, or Firm* — Linda Fox; Stephen Donovan; Debra Condino

(57) ABSTRACT

A soft prosthetic implant shell, such as a silicone breast implant shell, that has discrete fixation surfaces thereon for tissue adhesion. The fixation surfaces may be provided on the posterior face of the shell, as well as either on the periphery or at discrete areas on the anterior face. Band-shaped fixation surfaces may be provided on the anterior face of the shell to generally match the angle of pectoralis major or pectoralis minor muscle groups. The fixation surfaces may be roughened areas of the shell, or may be separate elements adhered to the shell.

15 Claims, 6 Drawing Sheets

(56) References Cited

U.S. PATENT DOCUMENTS

| | | |
|---|---|---|
| 4,329,385 A | 5/1982 | Banks |
| 4,428,082 A | 1/1984 | Naficy |
| 4,433,440 A | 2/1984 | Cohen |
| 4,470,160 A | 9/1984 | Cavon |
| 4,482,577 A | 11/1984 | Goldstein |
| 4,499,211 A | 2/1985 | Walch |
| 4,531,244 A | 7/1985 | Hamas |
| 4,573,999 A | 3/1986 | Netto |
| 4,592,755 A | 6/1986 | Penton |
| 4,610,690 A | 9/1986 | Tiffany |
| 4,636,213 A | 1/1987 | Pakiam |
| 4,643,733 A | 2/1987 | Becker |
| 4,648,880 A | 3/1987 | Brauman |
| 4,650,487 A | 3/1987 | Chaglassian |
| 4,651,717 A | 3/1987 | Jakubczak |
| 4,681,587 A | 7/1987 | Eberl |
| 4,772,285 A | 9/1988 | Ksander |
| 4,773,908 A | 9/1988 | Becker |
| 4,773,909 A | 9/1988 | Chaglassian |
| 4,790,848 A | 12/1988 | Cronin |
| 4,795,464 A | 1/1989 | Eberl |
| 4,803,025 A | 2/1989 | Brockmeyer |
| 4,828,560 A | 5/1989 | Heyler |
| 4,840,628 A | 6/1989 | Cavon |
| 4,841,992 A | 6/1989 | Sasaki |
| 4,859,383 A | 8/1989 | Dillon |
| 4,859,712 A | 8/1989 | Cox |
| 4,889,744 A * | 12/1989 | Quaid .................. 427/2.24 |
| 4,899,764 A | 2/1990 | Gauger |
| 4,902,294 A | 2/1990 | Gosserez |
| 4,906,423 A | 3/1990 | Frisch |
| 4,936,858 A | 6/1990 | O'Keeffe |
| 4,944,749 A | 7/1990 | Becker |
| 4,944,750 A | 7/1990 | Cox |
| 4,950,292 A | 8/1990 | Audretsch |
| 4,955,907 A | 9/1990 | Ledergerber |
| 4,955,909 A | 9/1990 | Ersek |
| 4,965,430 A | 10/1990 | Curtis |
| 4,969,899 A | 11/1990 | Cox |
| 5,002,572 A | 3/1991 | Picha |
| 5,007,929 A * | 4/1991 | Quaid .................. 623/8 |
| 5,007,940 A | 4/1991 | Berg |
| 5,011,494 A | 4/1991 | von Recum et al. |
| 5,022,942 A | 6/1991 | Yan |
| 5,026,394 A | 6/1991 | Baker |
| 5,034,422 A | 7/1991 | Triolo |
| 5,035,249 A | 7/1991 | Sasaki |
| 5,092,348 A | 3/1992 | Dubrul |
| 5,092,882 A | 3/1992 | Lynn |
| 5,104,409 A | 4/1992 | Baker |
| 5,116,387 A | 5/1992 | Berg |
| 5,135,959 A | 8/1992 | Hill |
| 5,146,933 A | 9/1992 | Boyd |
| 5,147,398 A | 9/1992 | Lynn |
| 5,158,571 A | 10/1992 | Picha |
| 5,158,573 A | 10/1992 | Berg |
| 5,171,269 A | 12/1992 | Bark |
| 5,185,297 A | 2/1993 | Park |
| 5,207,709 A | 5/1993 | Picha |
| 5,219,361 A | 6/1993 | von Recum et al. |
| 5,236,453 A | 8/1993 | Picha |
| 5,236,454 A | 8/1993 | Miller |
| 5,236,457 A | 8/1993 | Devanathan |
| 5,246,454 A | 9/1993 | Peterson |
| 5,282,856 A | 2/1994 | Ledergerber |
| 5,296,069 A | 3/1994 | Robert |
| 5,348,788 A | 9/1994 | White |
| 5,354,338 A | 10/1994 | Ledergerber |
| 5,358,521 A | 10/1994 | Shane |
| 5,376,117 A | 12/1994 | Pinchuk |
| 5,383,929 A | 1/1995 | Ledergerber |
| 5,437,824 A | 8/1995 | Carlisle |
| 5,441,919 A | 8/1995 | Park |
| 5,447,535 A | 9/1995 | Muller |
| 5,455,100 A | 10/1995 | White |
| 5,480,430 A | 1/1996 | Carlisle |
| 5,496,367 A | 3/1996 | Fisher |
| 5,496,370 A | 3/1996 | Hamas |
| 5,507,808 A | 4/1996 | Becker |
| 5,522,896 A | 6/1996 | Prescott |
| 5,525,275 A | 6/1996 | Iversen |
| 5,534,023 A | 7/1996 | Henley |
| 5,545,217 A | 8/1996 | Offray |
| 5,545,220 A | 8/1996 | Andrews |
| 5,549,671 A | 8/1996 | Waybright |
| 5,571,179 A | 11/1996 | Manders |
| RE35,391 E | 12/1996 | Brauman |
| 5,589,176 A | 12/1996 | Seare |
| 5,605,693 A | 2/1997 | Seare |
| 5,607,473 A | 3/1997 | Weber-Unger |
| 5,624,674 A | 4/1997 | Seare |
| 5,630,843 A | 5/1997 | Rosenberg |
| 5,630,844 A | 5/1997 | Dogan |
| 5,653,755 A | 8/1997 | Ledergerber |
| 5,658,330 A | 8/1997 | Carlisle |
| 5,674,285 A * | 10/1997 | Quaid .................. 623/8 |
| 5,681,572 A | 10/1997 | Seare |
| 5,776,159 A | 7/1998 | Young |
| 5,779,734 A | 7/1998 | Ledergerber |
| 5,798,065 A | 8/1998 | Picha |
| 5,824,081 A | 10/1998 | Knapp |
| 5,843,189 A | 12/1998 | Perouse |
| 5,855,588 A | 1/1999 | Young |
| 5,871,497 A | 2/1999 | Young |
| 5,895,423 A | 4/1999 | Becker |
| 5,935,164 A | 8/1999 | Iversen |
| 5,961,552 A | 10/1999 | Iversen |
| 5,964,803 A | 10/1999 | Iversen |
| 5,965,076 A | 10/1999 | Banks |
| 5,984,943 A | 11/1999 | Young |
| 6,071,309 A | 6/2000 | Knowlton |
| 6,083,262 A | 7/2000 | Caravel |
| 6,099,565 A | 8/2000 | Sakura |
| 6,113,634 A | 9/2000 | Weber-Unger |
| 6,146,418 A | 11/2000 | Berman |
| 6,183,514 B1 | 2/2001 | Becker |
| 6,187,043 B1 | 2/2001 | Ledergerber |
| 6,203,570 B1 | 3/2001 | Backe |
| 6,214,045 B1 | 4/2001 | Corbitt |
| 6,214,926 B1 | 4/2001 | Winn |
| 6,315,796 B1 | 11/2001 | Eaton |
| 6,387,133 B1 | 5/2002 | Perouse |
| 6,432,138 B1 | 8/2002 | Offray |
| 6,464,726 B1 | 10/2002 | Heljenek |
| 6,520,989 B1 | 2/2003 | Eaton |
| 6,531,523 B1 | 3/2003 | Davankov |
| 6,544,287 B1 | 4/2003 | Johnson |
| 6,602,452 B2 | 8/2003 | Schuessler |
| 6,605,116 B2 | 8/2003 | Falcon |
| 6,638,308 B2 | 10/2003 | Corbitt |
| 6,673,285 B2 | 1/2004 | Ma |
| 6,755,861 B2 | 6/2004 | Nakao |
| 6,802,861 B1 | 10/2004 | Hamas |
| 6,811,570 B1 | 11/2004 | Gehl |
| 6,818,673 B2 * | 11/2004 | Ferguson .................. 521/61 |
| 6,875,233 B1 | 4/2005 | Turner |
| 6,881,226 B2 | 4/2005 | Corbitt |
| 6,900,055 B1 | 5/2005 | Fuller |
| 6,916,339 B1 | 7/2005 | Missana |
| 6,921,418 B2 * | 7/2005 | Ledergerber .................. 623/11.11 |
| 6,932,840 B1 | 8/2005 | Bretz |
| 7,081,135 B2 * | 7/2006 | Smith et al. .................. 623/8 |
| 7,081,136 B1 | 7/2006 | Becker |
| 7,169,180 B2 | 1/2007 | Brennan |
| 7,192,450 B2 | 3/2007 | Brauker |
| 7,244,270 B2 | 7/2007 | Lesh |
| 7,323,208 B2 | 1/2008 | Ma |
| 7,476,249 B2 * | 1/2009 | Frank .................. 623/8 |
| 7,520,896 B2 | 4/2009 | Benslimane |
| 7,547,393 B2 | 6/2009 | Ramaswamy |
| 7,625,405 B2 | 12/2009 | Purkait |
| 7,632,228 B2 | 12/2009 | Brauker |
| 7,632,291 B2 | 12/2009 | Stephens |
| 7,641,688 B2 | 1/2010 | Lesh |

| | | | |
|---|---|---|---|
| 7,645,475 B2 | 1/2010 | Prewett | |
| 8,202,317 B2 | 6/2012 | Becker | |
| 8,313,527 B2* | 11/2012 | Powell et al. | 623/8 |
| 2001/0010024 A1* | 7/2001 | Ledergerber | 623/23.74 |
| 2002/0038147 A1* | 3/2002 | Miller, III | 623/8 |
| 2002/0143396 A1* | 10/2002 | Falcon et al. | 623/8 |
| 2002/0193885 A1 | 12/2002 | Legeay | |
| 2003/0036803 A1 | 2/2003 | McGhan | |
| 2003/0093151 A1 | 5/2003 | Zhang | |
| 2003/0205846 A1 | 11/2003 | Bellin et al. | |
| 2003/0208269 A1 | 11/2003 | Eaton | |
| 2004/0010225 A1 | 1/2004 | Schuessler | |
| 2004/0115241 A1 | 6/2004 | Calhoun | |
| 2004/0127985 A1* | 7/2004 | Bellin et al. | 623/8 |
| 2004/0143327 A1 | 7/2004 | Ku | |
| 2004/0148024 A1 | 7/2004 | Williams | |
| 2004/0153151 A1 | 8/2004 | Gonzales de Vicente | |
| 2004/0213986 A1 | 10/2004 | Kim | |
| 2005/0055093 A1 | 3/2005 | Brennan | |
| 2005/0070124 A1 | 3/2005 | Miller | |
| 2005/0122169 A1 | 6/2005 | Watanabe | |
| 2005/0216094 A1* | 9/2005 | Prewett | 623/23.74 |
| 2006/0036266 A1* | 2/2006 | Sulamanidze et al. | 606/151 |
| 2006/0036320 A1 | 2/2006 | Job | |
| 2006/0136056 A1 | 6/2006 | Wohl | |
| 2006/0224239 A1 | 10/2006 | Tiahrt | |
| 2006/0229721 A1* | 10/2006 | Ku | 623/8 |
| 2006/0235094 A1 | 10/2006 | Habibi-Naini | |
| 2006/0246121 A1 | 11/2006 | Ma | |
| 2007/0093911 A1 | 4/2007 | Fricke | |
| 2007/0104693 A1 | 5/2007 | Quijano | |
| 2007/0104695 A1 | 5/2007 | Quijano | |
| 2007/0116735 A1 | 5/2007 | Calhoun | |
| 2007/0135912 A1 | 6/2007 | Maxwell | |
| 2007/0154525 A1 | 7/2007 | Calhoun | |
| 2007/0190108 A1 | 8/2007 | Datta | |
| 2007/0198085 A1 | 8/2007 | Benslimane | |
| 2008/0009830 A1 | 1/2008 | Fujimoto | |
| 2008/0071371 A1 | 3/2008 | Elshout | |
| 2008/0154366 A1 | 6/2008 | Frank | |
| 2008/0241212 A1 | 10/2008 | Moses | |
| 2008/0268019 A1 | 10/2008 | Badylak | |
| 2008/0312739 A1 | 12/2008 | Agerup | |
| 2009/0045166 A1 | 2/2009 | Li | |
| 2009/0082864 A1 | 3/2009 | Chen | |
| 2009/0087641 A1 | 4/2009 | Favis | |
| 2009/0093878 A1 | 4/2009 | Glicksman | |
| 2009/0118829 A1 | 5/2009 | Powell | |
| 2009/0125107 A1* | 5/2009 | Maxwell | 623/8 |
| 2009/0148829 A1 | 6/2009 | Ecker | |
| 2009/0169716 A1 | 7/2009 | Linhardt | |
| 2009/0198331 A1* | 8/2009 | Kesten et al. | 623/8 |
| 2009/0198332 A1 | 8/2009 | Becker | |
| 2009/0198333 A1* | 8/2009 | Becker | 623/8 |
| 2009/0254179 A1* | 10/2009 | Burnett | 623/8 |
| 2010/0042211 A1 | 2/2010 | Van Epps et al. | |
| 2010/0292790 A1 | 11/2010 | Stroumpoulis et al. | |
| 2011/0035004 A1* | 2/2011 | Maxwell | 623/8 |
| 2011/0054605 A1 | 3/2011 | Becker | |
| 2011/0093069 A1 | 4/2011 | Goraltchouk et al. | |
| 2011/0106249 A1 | 5/2011 | Becker | |
| 2011/0117267 A1 | 5/2011 | Powell et al. | |
| 2011/0184531 A1 | 7/2011 | Goraltchouk et al. | |
| 2011/0196488 A1 | 8/2011 | Goraltchouk et al. | |
| 2011/0196489 A1 | 8/2011 | Van Epps et al. | |
| 2011/0276133 A1 | 11/2011 | Liu et al. | |
| 2011/0276134 A1 | 11/2011 | Manesis et al. | |
| 2011/0278755 A1 | 11/2011 | Liu et al. | |
| 2011/0282444 A1 | 11/2011 | Liu et al. | |
| 2011/0309541 A1 | 12/2011 | Thompson et al. | |
| 2011/0313073 A1 | 12/2011 | Goraltchouk et al. | |
| 2012/0004722 A1 | 1/2012 | Goraltchouk et al. | |
| 2012/0041555 A1 | 2/2012 | Manesis et al. | |
| 2012/0077010 A1 | 3/2012 | Manesis et al. | |
| 2012/0077012 A1 | 3/2012 | Liu et al. | |
| 2012/0077891 A1 | 3/2012 | Liu et al. | |
| 2012/0101574 A1 | 4/2012 | Goraltchouk et al. | |
| 2012/0142798 A1 | 6/2012 | Thompson et al. | |
| 2012/0321777 A1 | 12/2012 | Stroumpoulis et al. | |
| 2013/0013062 A1 | 1/2013 | Thompson et al. | |
| 2013/0023987 A1 | 1/2013 | Liu et al. | |
| 2013/0032962 A1 | 2/2013 | Liu et al. | |
| 2013/0053956 A1 | 2/2013 | Powell et al. | |

FOREIGN PATENT DOCUMENTS

| | | |
|---|---|---|
| EP | 1532942 A1 | 5/2005 |
| JP | 2003-062062 | 4/2003 |
| JP | 2007-029717 | 8/2007 |
| WO | 98-10803 | 3/1998 |
| WO | 00-24437 | 5/2000 |
| WO | 2004-037318 | 5/2004 |
| WO | 2004-062531 | 7/2004 |
| WO | WO 2006/133366 A1 | 12/2006 |
| WO | 2009-061672 | 5/2009 |
| WO | 2009-110917 | 9/2009 |
| WO | 2011-094155 | 8/2011 |
| WO | 2011-097499 | 8/2011 |

OTHER PUBLICATIONS

Brohim, Robert et al, 1992, Early Tissue Reaction to Textured Breast Implant Surfaces, Ann Plast Surg, 28, 354-362.

Eliza Minami, 2006, The Composition and Behavior of Capsules Around Smooth and Textured Breast Implants in Pigs, Plast. Reconstr. Surg., 118, 874-884.

Guobao Wei et al, 2006, Macroporous and Nanofibrous Polymer Scaffolds and Polymer/Bone-Like Apatite Composite Scaffolds Generated by Sugar Spheres, Journal of Biomedical Materials Research, 78A, 306-315.

Inamed Aesthetics Brochure, Directions for Use Style 410 Silicone-Filled Breast Implants (2003).

Peter Ma, 2004, Scaffolds for tissue fabrication, Materials Today, 7, 30-40.

Philip Barnsley et al, 2006, Textured Surface Breast Implants in the Prevention of Capsular Contracture Among Breast Augmentation Patients: A Meta-Analysis of Randomized Controlled Trials, Plastic and Reconstructive Surgery, 117(7), 2182-2190.

S. Barr et al, 2009, Current Implant Surface Technology: An Examination of Their Nanostructure and Their Influence on Fibroblast Alignment and Biocompatibility, Elastic, 9, 198-217.

Sonia Alvarez et al, 2007, Synthesis of Macro/Mesoporous Silica and Carbon Monoliths by Using a Commercial Polyurethane Foam as Sacrificial Template, Material Letters, 61, 2378-2381.

William L. Murphy, et al., 2002, Salt Fusion: An Approach to Improve Pore Interconnectivity Within Tissue Engineering Scaffolds, Tissue Engineering, 8 (1), 43-52.

Yuan Zhang, 2009, Macroporous Alumina Monoliths Prepared by Filling Polymer Foams with Alumina Hydrogels, Journal of Materials Science, 44, 931-938, Springer Science.

* cited by examiner

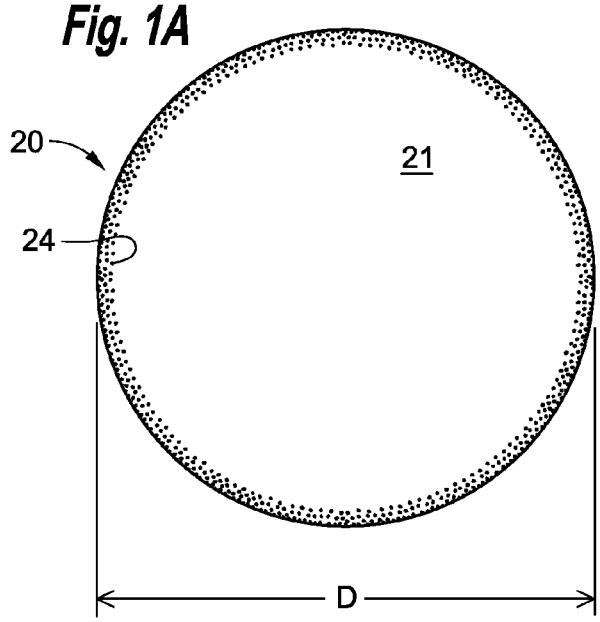
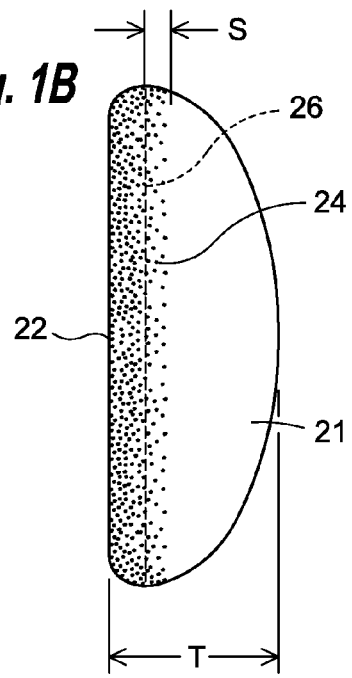
Fig. 1A   Fig. 1B
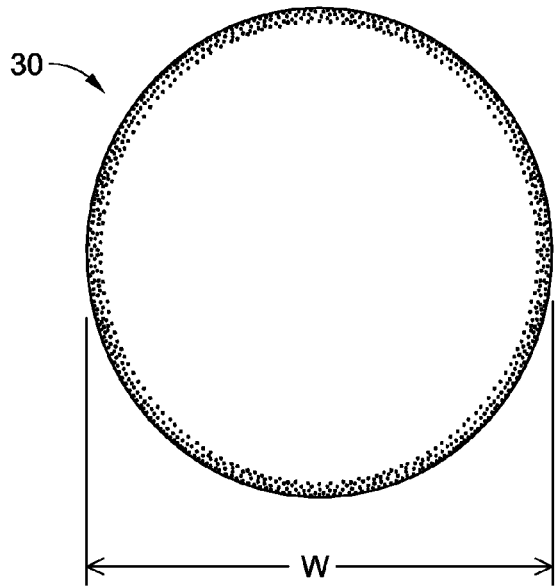
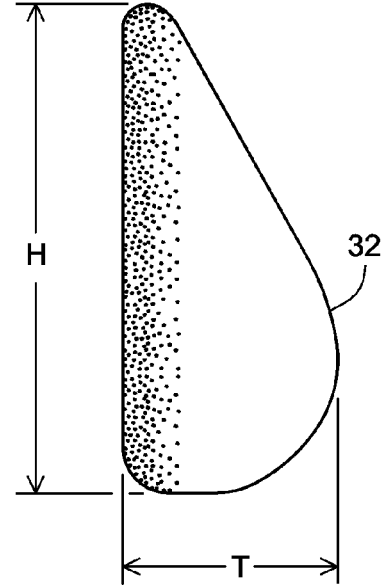
Fig. 2A   Fig. 2B

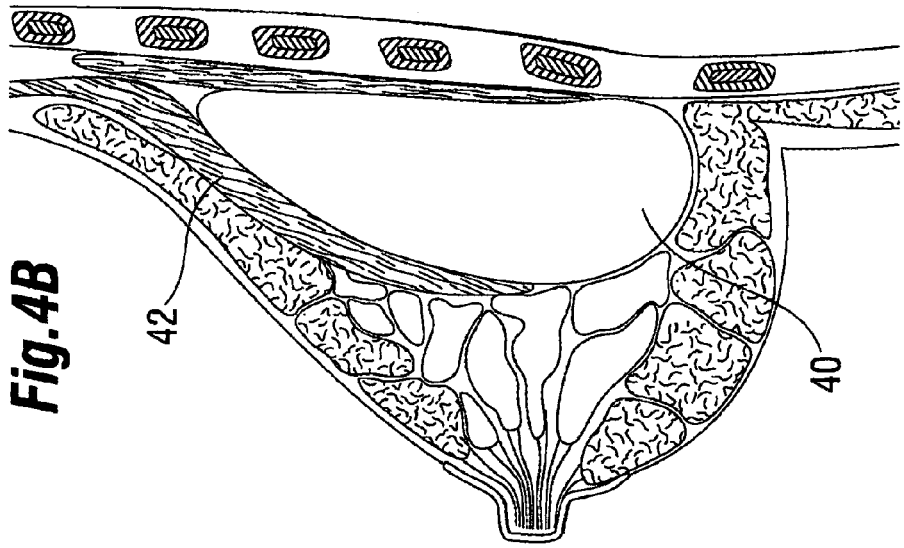
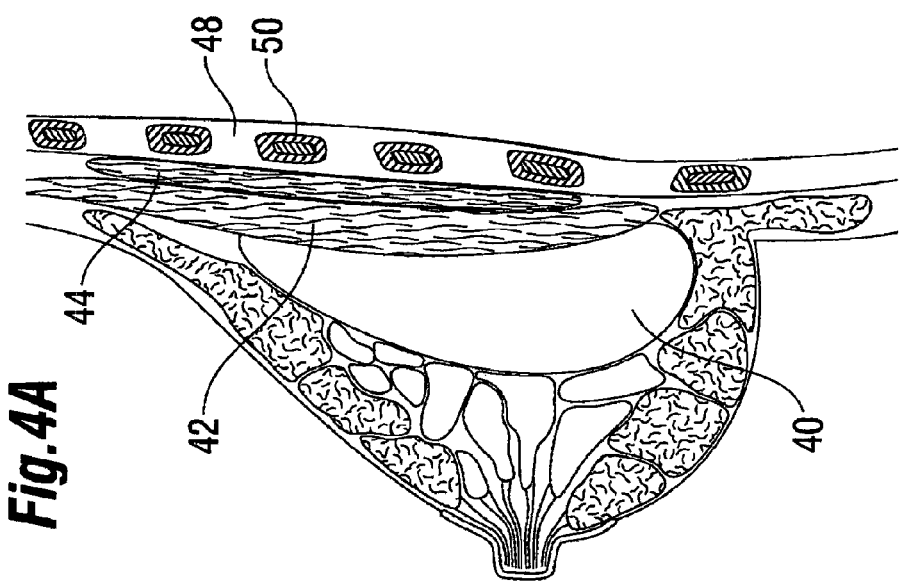

SOFT FILLED PROSTHESIS SHELL WITH DISCRETE FIXATION SURFACES

CROSS REFERENCE

This application claims the benefit of U.S. Provisional Patent Application Ser. No. 61/088,418, filed on Aug. 13, 2008, the entire disclosure of which is incorporated herein by this specific reference.

FIELD OF THE INVENTION

The present invention relates to soft prosthetic implants and, more particularly, to textured exterior surfaces of such implants, for instance, breast implants.

BACKGROUND OF THE INVENTION

Implantable prostheses are commonly used to replace or augment body tissue. In the case of breast cancer, it is sometimes necessary to remove some or all of the mammary gland and surrounding tissue, which creates a void that can be filled with an implantable prosthesis. The implant serves to support surrounding tissue and to maintain the appearance of the body. The restoration of the normal appearance of the body has an extremely beneficial psychological effect on post-operative patients, eliminating much of the shock and depression that often follows extensive surgical procedures. Implantable prostheses are also used more generally for restoring the normal appearance of soft tissue in various areas of the body, such as the buttocks, chin, calf, etc.

Soft implantable prostheses typically include a relatively thin and flexible envelope or shell made of vulcanized (cured) silicone elastomer. The shell is filled either with a silicone gel or with a normal saline solution. The filling of the shell takes place before or after the shell is inserted through an incision in the patient.

In the United States, women can choose between two different types of breast implant shell surfaces: a smooth surface and a textured surface. The surgeon generally recommends the type of surface based on his or her technique and the shape of the breast implant chosen to best fit the needs of each patient.

Breast implants are not without complications, one of which is termed capsular contracture. This is a complication that occurs upon contraction of a fibrous outer capsule that forms around the implant, which tends to render the implant spherical and stiff and aesthetically undesirable. According to the United States Food and Drug Administration's (FDA) Breast Implant Consumer Handbook (2004), the literature shows that textured surface breast implants may decrease the capsular contracture rate.

Texturing may be provided in a number of ways. Silicone gel breast implants covered with a thin layer of textured polyurethane foam enjoyed considerable popularity in the 1980s because of their remarkable resistance to the early development of fibrous capsular contracture. For example, U.S. Pat. No. 3,293,663 describes a soft gel-filled prosthesis with a porous polyester fabric on the back side for tissue ingrowth and anchoring to the chest wall. Although these devices are no longer available in the U.S. because of regulatory constraint, their medical and commercial success stimulated interest in surface texturization of silicone implants.

Despite many advances in the development of safe and comfortable prosthetic implants, there remains room for improvement.

SUMMARY OF THE INVENTION

The present invention provides a prosthesis suitable for implantation in a human being, for example, a breast implant suitable for use in reconstruction or augmentation of the human breast. The prosthesis generally comprises an implantable member, for example, an elastomeric shell that is filled or is fillable with a liquid or gel. The implantable member has an exterior surface including one or more fixation regions defined thereon and configured, positioned or structured to provide enhanced or controlled tissue ingrowth or adhesion.

In accordance with one aspect of the invention, the fixation surfaces are discrete, generally elongated surface portions extending across an anterior face or a posterior face of the implant. These fixation surfaces, sometimes herein referred to as "fixation regions", are generally defined by a texture, roughness or sheen that is different from a texture, roughness or sheen of adjacent surface portions of the implant.

In some embodiments, the fixation regions have an increased or enhanced texture relative to the balance of the anterior face or posterior face of the implant. In other words, the balance of the exterior surface may be relatively less textured than the fixation regions. In some embodiments, the fixation regions are textured and adjacent surfaces, for example, the surface or surfaces that are not defined by the fixation regions, are substantially less textured, or are relatively smooth.

The prosthesis may be structured to encourage enhanced tissue ingrowth or adhesion at the fixation regions, relative to an otherwise identical surface without such texture, roughness or sheen.

In one aspect of the invention, the fixation regions are positioned and/or configured such that the prosthesis, after implantation in the body, moves more naturally with the human body, for example, in relative unity with the muscles of the body. It is contemplated that because the implant moves more naturally with the human body, the implant may be less prone to wear resulting from material stresses relative to conventional implants, for example, implants without such fixation regions. Furthermore, it is contemplated that the present implants will be more comfortable to the patient in that they will move more naturally with the body.

In a more specific aspect of the invention, the fixation regions may be located at specific regions on an anterior face of the shell, that is, a face of the shell which faces the front of the human body when the implant has been appropriately implanted in the human body. Alternatively or additionally, one or more discrete fixation surface may be provided on a periphery of the shell (e.g. circumferentially) and/or on the posterior face of the shell, that is, the face of the shell that faces the back of the human body when the implant has been implanted in the human body.

In an even more specific aspect of the invention, the fixation regions comprise at least one elongated region located on the anterior face of the shell. The at least one elongated region may be, for example, a band-shaped region or alternatively, a plurality of band shaped regions having enhanced texture, roughness or sheen.

The elongated fixation regions may be positioned to align with one of the pectoralis major muscle groups or pectoralis minor muscle groups of the human body when the implant is implanted in the body. For example, in one embodiment of the invention, the at least one elongated region comprises a diagonally positioned band shaped region intended to align with the pectoralis major muscle group when the implant has been implanted in the body. In another embodiment, the at least one fixation region comprises a plurality of elongated regions in a radiating configuration generally copying the positioning of the pectoralis minor muscle group wherein the implant has been implanted in the body.

In another broad aspect of the invention, the prosthesis comprises a breast implant having a shell including a fixation region having a first texture and a balance of the shell surface having a second texture that is different from the first texture. In other words, in some embodiments of the invention, the entire, or substantially entire, exterior of the breast implant shell is a textured surface with specific regions thereof having a greater degree of texturing relative to the remaining portions of the textured surface.

It is contemplated that such different texturing will stimulate or encourage different degrees of tissue ingrowth or adhesion at the different fixation regions. For example, in one embodiment, the first fixation region is located on a posterior face of the implant and the second fixation region is located on an anterior face of the implant. The first fixation region may be defined by a texture that is more conducive to tissue interaction and adhesion whereas the second fixation region may be defined by a texture that is relatively less conducive to tissue interaction and adhesion.

In yet another aspect of the invention, the prosthesis comprises a shell having an exterior structured to contact tissue, the shell including a first fixation surface having a first open cell structure, and a second fixation surface having a second open cell structure different than said first open cell structure. In addition, the first fixation surface and the second fixation surface are positioned to encourage respectively different degrees of tissue ingrowth or tissue adhesion by the body at a body-shell interface.

For example, the first open cell structure comprises relatively large open cells and the second open cell structure comprises relatively smaller open cells. Alternatively or additionally, the first open cell structure may comprise a first distribution of cells and the second open cell structure comprises a second distribution of cells wherein the first distribution of cells is relatively more dense than the second distribution of cells.

In yet another specific aspect of the invention, the first open cell structure comprises relatively large rounded open cells and the second open cell structure comprises relatively small rounded open cells. Alternatively, the first open cell structure comprises relatively rounded open cells and the second open cell structure comprises relatively angular open cells.

Advantageously, in accordance with certain embodiments, the first and second fixation surfaces are positioned and structured to be at least somewhat effective to disrupt or disorient capsular tissue formation about the prosthesis after the prosthesis has been implanted in the body.

The present invention further provides a breast prosthesis shell for implantation in a human being, the shell manufactured by the steps of providing a shell precursor; applying a layer of silicone elastomer to the shell precursor, applying solid particles of a first configuration to a portion of the layer of silicone elastomer and applying solid particles of a second configuration to another portion of the layer of silicone elastomer before the layer is fully cured. After the layer including the solid particles embedded therein is cured, the solid particles are then dissolved, for example, by means of a solvent that does not dissolve the silicone elastomer to any appreciable extent. The resulting elastomer shell includes a first open cell texture region formed by said application of the solid particles of the first configuration, and a second open cell texture region formed by said application of the solid particles of the second configuration.

In yet another aspect of the invention, a method of augmenting or reconstructing a breast of a human being is provided. The method generally comprises providing an implantable member including at least one elongated fixation region as described elsewhere herein and implanting the implantable member into a breast of a human being such that the fixation region generally aligns with one of the pectoralis major muscle group and the pectoralis minor muscle group. The method may further comprise filling the implantable member with a liquid or gel prior to or after the implanting step.

A further understanding of the nature and advantages of the present invention are set forth in the following description and claims, particularly when considered in conjunction with the accompanying drawings in which like parts bear like reference numerals.

BRIEF DESCRIPTION OF THE DRAWINGS

Features and advantages of the present invention will become appreciated as the same become better understood with reference to the specification, claims, and appended drawings wherein:

FIGS. 1A-1B are anterior or front and side elevational views of an exemplary round breast implant of the present invention having rear and peripheral fixation surfaces;

FIGS. 2A-2B are front and side elevational views of an exemplary shaped breast implant of the present invention having rear and peripheral fixation surfaces;

FIGS. 4A and 4B are vertical sectional views through a woman's breast and adjacent chest anatomy showing, respectively, subglandular and submuscular placement of a breast implant;

DETAILED DESCRIPTION

Figure 3B:
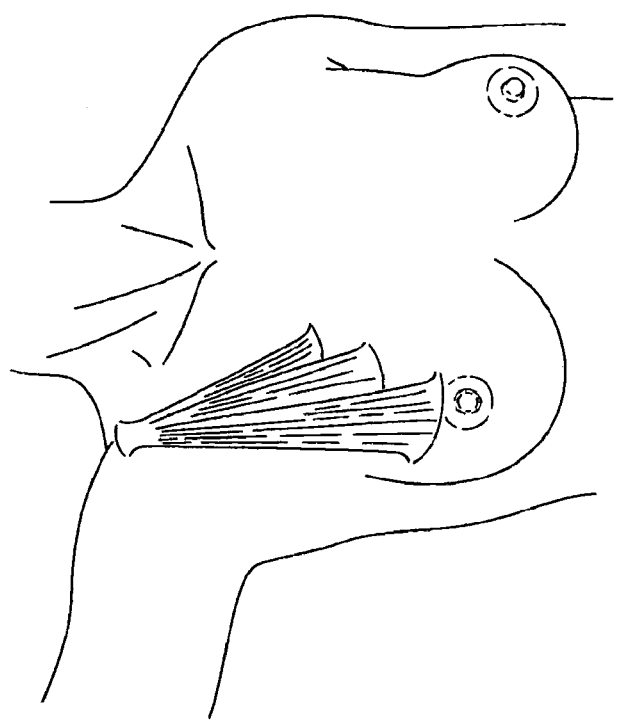
FIGS. 3A and 3B are schematic views of a woman's upper torso showing, respectively, pectoralis major and pectoralis minor muscle positions on one side.

The present invention provides a saline- or gel-filled soft implant shell, preferably a silicone elastomer shell, with a fixation surface over an exterior portion. The primary application for such soft implants is to reconstruct or augment the female breast. Other potential applications are implants for the buttocks, testes, or calf, among other areas.

The term fixation surface refers to a surface on the exterior of the implant shell adapted to encourage tissue ingrowth or adhesion. A fixation surface may be a roughened or textured area in comparison to other smooth or less textured areas of the implant shell. The number of textured surfaces are known in the art, including those described above in the background section. For example, a textured surface may be formed by a salt removal process, such as with the Allergan BIOCELL® surface. Other configurations of fixation surfaces include textured separate elements such as patches or films adhered to the outside of the implant, as well as a roughened surface features formed during the mold process. One exemplary method is to roughen the interior surface of the mold in which the implant shell is formed. Another method is to roughen the exterior of the implant after formation. The present invention should not be considered limited to any particular type of texturing or fixation surface, though there might be certain advantages with one or more of these techniques.

Previous breast implants have been formed with either all smooth or all textured shells. Some of the prior art designs also described placing textured surfaces on the posterior or rear of the implant to encourage adhesion to the chest wall. To date, particular placement of discrete fixation surfaces on the periphery or front side of breast implants has not been described in the art. The present invention illustrates a number of different configurations, but those of skill in the art will understand that other shapes and placements are possible, and that the invention should be limited only by the appended claims.

FIGS. 1A-1B are front and side elevational views of an exemplary round breast implant 20 of the present invention having a generally smooth exterior except for posterior or rear 22 and peripheral 24 fixation surfaces. Alternatively, the exterior surface of the implant may have less textured areas outside of the fixation surfaces 22, 24, such as a fine textured or matte finish, or a combination of smooth and textured areas. Indeed, the fixation surfaces 22, 24 themselves may have differing degrees of texturing. In this embodiment, the fixation surfaces 22, 24 are illustrated with stippling, which is representative of either roughness from a salt removal process or from a roughened mold. Of course, the fixation surfaces 22, 24 may also be formed by other means, such as for example with a separate fabric or foam layer adhered to the implant 20. The diameter D and front-to-back thickness T of the implant are shown and vary depending on the patient's chest size and aesthetic considerations.

Desirably, the rear fixation surface 22 extends to the apex 26 or generatrix of the convex outer periphery of the implant 20. The peripheral fixation surface 24 continues forward a short distance S around the anterior or front surface of the implant. In a preferred embodiment, the distance S is between about 10-30% of the front-to-back thickness T. Preferably, the peripheral fixation surface 24 extends completely around the periphery of the implant 20, therefore rendering the round implant 20 completely axi-symmetric. However, the peripheral fixation surface 24 may be abbreviated so as to extend around only a portion of the periphery of the implant, such as the inferior or superior half, or may be broken up into spaced segments. In one embodiment, the peripheral fixation surface 24 is broken up to evenly spaced segments resulting in alternating smooth and textured areas such that the implant 20 is substantially axi-symmetric and the surgeon need not bother with any particular implant orientation.

FIGS. 2A-2B illustrate a shaped breast implant 30 of the present invention having an inferior frontal lobe 32 simulating a natural breast. The implant 30 includes a rear fixation surface 34 and a peripheral fixation surface 36, as in the embodiment of FIGS. 1A-1B. The width W, height H, and front-to-back thickness T of the implant are shown. If the front projection is round, then W=H, otherwise W may be greater than or less than H. When provided with a natural shape, the implant 30 has a proper orientation, namely with the inferior lobe 32 at the lower center. Accordingly, the peripheral fixation surface 36 may extend completely around the periphery of the implant, or may be formed in discrete areas and be oriented relative to the natural shape of the implant. For example, the peripheral fixation surface 36 may be formed only around the inferior or lower half of the implant, or may be formed only on the sides. Proper placement of the implant 30 based on its natural shape will therefore simultaneously properly place the discrete fixation surfaces.

Figure 3A:
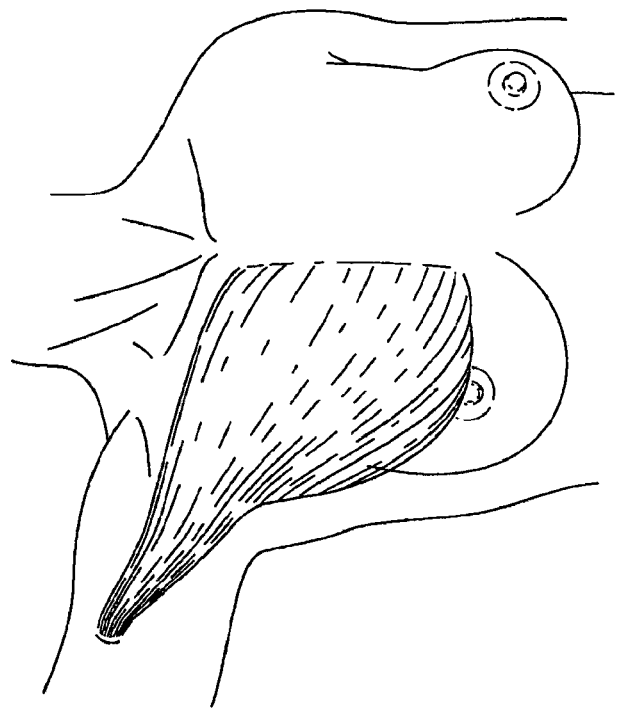

FIG. 3A illustrates a woman's upper torso schematically showing on one side placement of the pectoralis major muscle group, while FIG. 3B illustrates the pectoralis minor muscle group. These two most groups overlap one another and extend generally from the shoulder or collarbone region to the rib cage underneath the breast. One aspect of the present invention is to provide fixation surfaces aligned with these muscle groups. The points or lines of contact of the implant with the primary chest muscles experience greater movement than other areas, and thus it is believed that a fixation surface coincident with or aligned with one or more of these muscle groups is more likely to remain secured (i.e., they move with the muscle).

FIG. 4A is a vertical sectional view through a woman's breast and adjacent chest anatomy showing a subglandular placement of a breast implant 40. The implant 40 is positioned over the top of the pectoralis major muscle group 42, which in turn overlays the pectoralis minor muscle group 44. The chest wall 48 showing a plurality of ribs 50 is also indicated underneath the pectoralis minor muscle 44. FIG. 4B is a vertical sectional view as in FIG. 4A but showing a submuscular placement of the implant 40, underneath the pectoralis major muscle group 42. Both these two implant placements are utilized primarily depending on the surgeon's clinical determination, sometimes influenced by a dialogue between patient and the surgeon and desired outcome. Depending on the implant placements, the implant 40 may be in contact with one or both muscle groups.

Figure 5A:
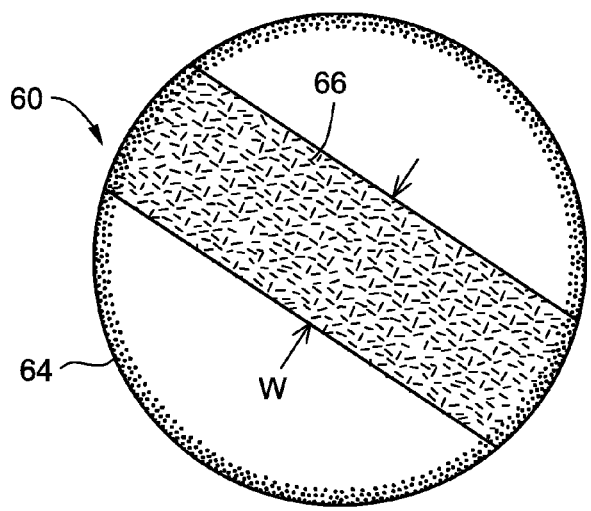
FIGS. 5A-5B are front and side elevational views of an exemplary round breast implant of the present invention having rear and peripheral fixation surfaces as well as a frontal band-shaped fixation surface.
Figure 5B:
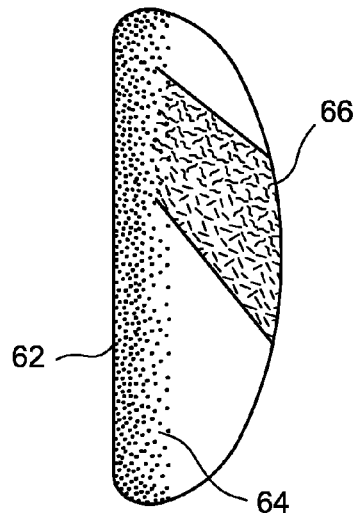

FIGS. 5A-5B are front and side elevational views of an exemplary round breast implant 60 of the present invention having a rear fixation surface 62, a peripheral fixation surface 64, and a frontal band-shaped fixation surface 66. The band-shaped fixation surface 66 extends generally along a diagonal angle and commences at the front border of the peripheral fixation surface 64. The illustrated embodiment, the fixation surface 66 has a constant width W as seen from the front in FIG. 5A. In one embodiment, the width W is between about 1 mm to about 20 mm, for example, between about 2 mm to about 15 mm. Alternatively, the front view of the fixation surface 66 may be other than a constant width, and may have non-linear boundaries.

In one embodiment, the band-shaped fixation surface 66 is generally oriented with either the pectoralis major muscle group or pectoralis minor muscle group. For instance, if the implant 60 is destined for a submuscular placement such as in FIG. 4B, the fixation surface 66 may be oriented to be generally aligned with the pectoralis major muscle group, as seen in FIG. 3A. Alternatively, the angle at which the insertion surface 66 is oriented may be an approximation of the average angle of the pectoralis major and pectoralis minor muscle groups. In this way, the implant 60 has a fixation surface 66 to encourage tissue ingrowth or adhesion along the major stress lines of the implant. Preferably, the fixation surface 66 is angled between about 30-60° with respect to a vertical plane through the implant 60. Of course, if the implant 60 is round as shown, the fixation surface 66 itself defines the orientation thereof. In one embodiment, the band-shaped fixation surface 66 is centered about the center of the implant 60, therefore creating two symmetric orientations about 180° apart. This arrangement facilitates implant by providing two possible orientations for the surgeon.

The band-shaped fixation surface 66 is shown as having a different composition than either the rear fixation surface 62 or peripheral fixation surface 64. In this respect, any of the different fixation surfaces described herein may be formed in the same way, or using different techniques. For instance, the fixation surfaces 62, 64 may be texturing in the implant shell, while the band-shaped fixation surface 66 is a separate element such as a patch or film adhered to the front surface of the implant. The reader will understand that all combinations of the various fixation surface inclusions, placements and types are contemplated. Likewise, any of these potential combinations may be provided on any of the various round or shaped implants as shown, or others not shown. For instance, fixation surfaces may also be useful for implants for the buttocks, testes, or calf, among other areas, and may be aligned with muscle groups in those areas.

Figure 6A:
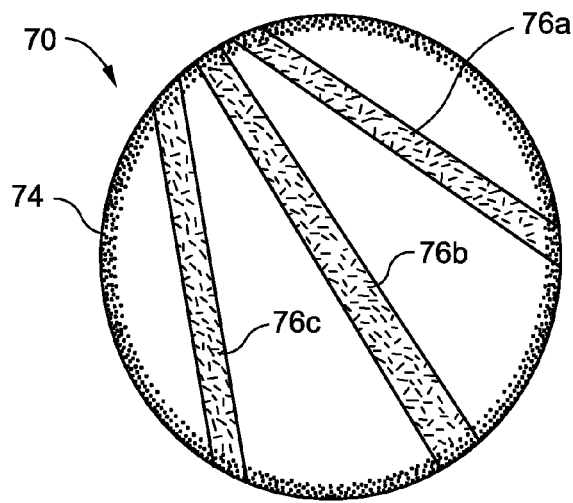
FIGS. 6A-6B are front and side elevational views of an exemplary shaped breast implant of the present invention having rear and peripheral fixation surfaces as well as frontal band-shaped fixation surfaces.
Figure 6B:
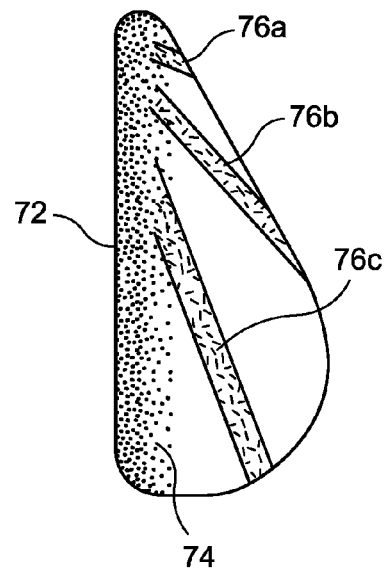

FIGS. 6A-6B illustrate an exemplary shaped breast implant 70 of the present invention. The implant 70 again features a rear fixation surface 72, a peripheral fixation surface 74, and a plurality of separate band-shaped fixation surfaces 76a, 76b, 76c. These discrete fixation surfaces 76a, 76b, 76c desirably mimic one or more of the muscle groups described above. For example, the three fixation surfaces 76a, 76b, 76c may be generally oriented relative to the fan-shaped pectoralis minor muscle group. Because the shaped implant 70 is orientation-specific, proper placement of the implant automatically orients the fixation surfaces 76a, 76b, 76c with the particular muscle group. As mentioned above, the various fixation surfaces 72, 74, 76a, 76b, and 76c may be formed with a similar level of roughness, or some may be less textured, such as with a matte finish. For instance, the rear and peripheral fixation surfaces 72, 74 may have a fine, matte finish, while the frontal fixation surfaces 76a, 76b, 76c are more densely textured. The present invention contemplates all permutations of texturing choices.

In cross-section, the textured implant shells of the present invention may be single- or multi-layered. The overall thickness of the textured implant shell wall may be somewhat greater than a similar smooth-walled shell because of the extra layers of texture.

Figure 7:
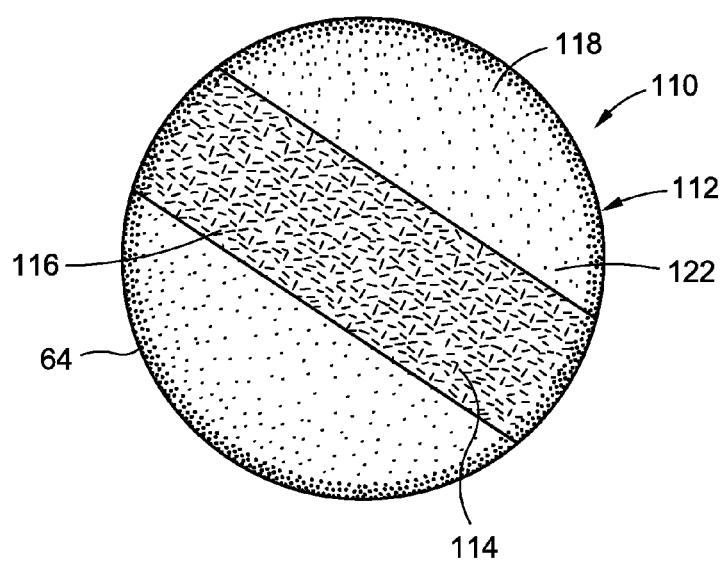
FIG. 7 is a front elevational view of another breast implant in accordance with the invention including a first fixation region having a first texture and a second fixation region having a second texture different from the first texture.

Turning now to FIG. 7, an anterior (front) view of another breast implant of the present invention is shown generally at 110. The implant 110 includes a shell 112 having an exterior surface including a first fixation region 114 having a first texture 116 and a second fixation region 118 having a second texture 122 that is different from the first texture 116. In the shown embodiment, the first texture 116 is a more "aggressive" texture than the second texture 122. The first texture 116 is structured to encourage a greater degree of tissue interaction than the second texture 122.

In lieu of the second texture 122, it is contemplated that the second fixation region 118, and perhaps the entire balance of the exterior of the shell 112, may be a low sheen surface, for example, a matte finish.

Figure 8A:
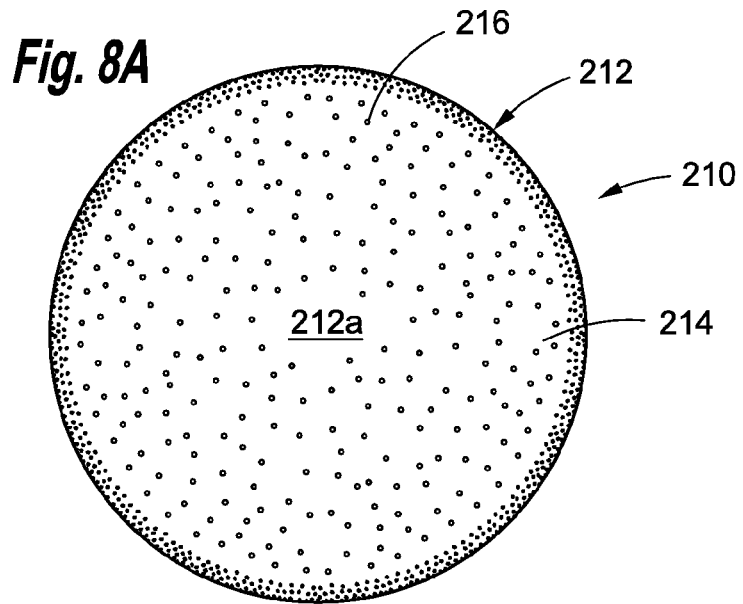
FIGS. 8A and 8B are front and rear elevational views of an exemplary round breast implant of the present invention having a front texture and a rear texture that are different from one another.
Figure 8B:
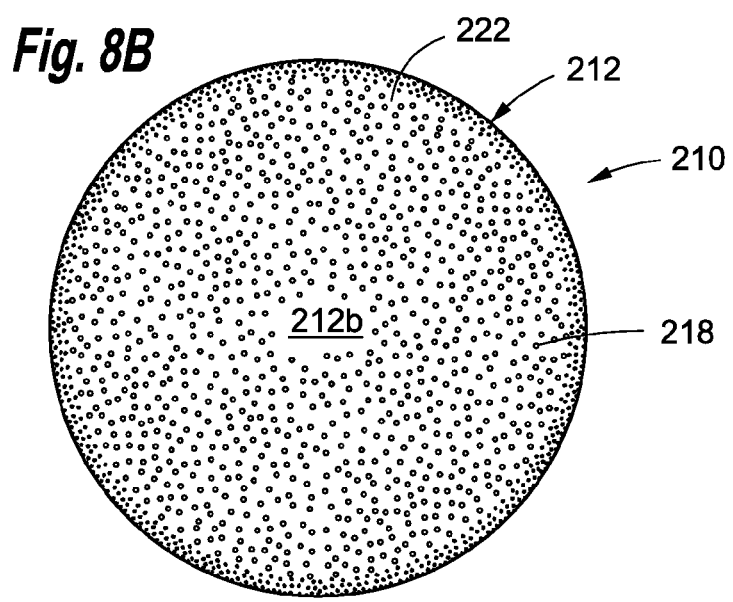

Turning now to FIGS. 8A and 8B, anterior (front) and posterior (rear) views, respectively, of another breast implant in accordance with the invention are shown generally at 210. The implant 210 includes a shell 212 having an anterior face 212a and a posterior face 212b, and including a first fixation region 214 having a first texture 216 and a second fixation region 218 having a second texture 222 that is different from the first texture 216. In the shown embodiment, the first texture 216 may encompass the entire, or substantially entire, anterior face 212a of the implant 210. The first texture 216 is defined by a first distribution of pores, crevices or caverns that is relatively less dense than that of the second texture 222. The second texture 222, which may encompass the entire, or substantially entire, posterior face 221b of the implant 210, may be structured to encourage a greater degree of tissue interaction and adhesion than that of the first texture 216.

The shells 112 and 212 may be manufactured by a method of the invention comprising the steps of providing a shell precursor; applying a layer of silicone elastomer to the shell precursor, applying solid particles of a first configuration to a portion of the layer of silicone elastomer and applying solid particles of a second configuration to another portion of the layer of silicone elastomer before the layer is fully cured. After the layer including the solid particles embedded therein is cured, the solid particles are then dissolved, for example, by means of a solvent that does not dissolve the silicone elastomer to any appreciable extent. The resulting elastomer shell includes a first open cell texture region formed by said application of the solid particles of the first configuration, and a second open cell texture region formed by said application of the solid particles of the second configuration.

One process for forming flexible implant shells for implantable prostheses involve dipping a suitably shaped mandrel into a silicone elastomer dispersion. Many such dispersions are used in the field. Basically they contain a silicone elastomer and a solvent. The silicone elastomer is typically polydimethylsiloxane, polydiphenyl-siloxane or some combination of these two. Typical solvents include xylene or 1,1,1-trichloroethane. Different manufacturers vary the type and amount of the ingredients in the dispersion, the viscosity of the dispersion and the solid content of the dispersion. Nonetheless, the present invention is expected to be adaptable to have utility with a wide variety of silicone rubber dispersions.

The mandrel is withdrawn from the dispersion and the excess silicone elastomer dispersion is allowed to drain from the mandrel. After the excess dispersion has drained from the mandrel at least a portion of the solvent is allowed to volatilize or evaporate. Normally this is accomplished by flowing air over the coated mandrel at a controlled temperature and humidity. Different manufacturers use various quantities, velocities or directions of air flow and set the temperature and humidity of the air at different values. However, the desired result, driving off the solvent, remains the same.

It is also common for prostheses manufacturers to repeat this dip and volatilize procedure a number of times so that a number of layers are built up on the mandrel to reach a desired shell thickness. A layered structure like most current silicone elastomer shells can be made by sequentially dipping the mandrel in different dispersions. Alternatively, the steps may be repeated in a single dispersion so that the finished product is a single homogenous material or layer. That is, the dipping process may be done in multiple stages or steps, each step adding more material, yet the finished product exhibits no distinct layers and the entire shell wall is homogenous or uniform in composition.

An exemplary process for forming the fixation surfaces on either a multi-layered shell or a single-layered shell will now be described. After the mandrel is raised out of the dispersion with what is to be the final layer adhering thereto, this layer is allowed to stabilize. That is, it is held until the final coating no longer flows freely. This occurs as some of the solvent evaporates from the final coating, raising its viscosity.

Again, it should be understood that alternative methods are contemplated for forming the flexible shell prior to the texturing process. The dip molding process advantageously results in the flexible shell pre-mounted on a dipping mandrel, which can then be used for the texturing process. However, if the flexible shell is made by another technique, such as by rotational molding, it can subsequently be mounted on a dipping mandrel and the process continued in the same manner.

Once the flexible shell has been stabilized and mounted on the mandrel, any loose fibers or particles are removed from the exterior of the shell, for example, with an anti-static air gun. A tack coat layer is then applied. The tack coat layer may be sprayed on, but is desirably applied by dipping the flexible shell on the mandrel into a tack coat dispersion. The operator immerses the flexible shell into the dispersion and returns the mandrel to a rack for stabilization. The time required for stabilization typically varies between 5-20 minutes. A suitable tack coat layer is desirably made using the same material employed in the base layers.

At this point, granulated solid particles (i.e., salt crystals) are applied over that portion of the exterior surface that will end up as the fixation surface. The solid particles may be applied manually by sprinkling them over the surface while the mandrel is manipulated, or a machine operating like a bead blaster or sand blaster could be used to deliver a steady stream of solid particles at an adequate velocity to the coating on the mandrel. However, a preferred method of solid particle application is to dip the mandrel/shell into a body of the solid particles or expose it to a suspension of the solid particles. It should be understood that the present invention is not intended to be restricted to any one particular method of applying particles. One possible method to apply solid particles to some but not all of the shell is to mask off areas of the shell for which particles are not to be applied and then apply the particles to the non-masked areas.

The tacky flexible shell may then be immersed in a fluidized (air-mixing) aqueous salt bath having regular cubic salt crystals between about 10 to about 600 microns, or round crystals between about 50-2000 microns or a combination thereof. Varying degrees of texturing may be formed with the salt removal process by using differently sized or shaped salt granules (for example, round salt crystals versus angular salt crystals, large salt crystals versus relatively small salt crystals, high density distribution of salt crystals versus relatively low density distribution of salt crystals), on different areas of the shell. The shell is rotated for even coverage, removed, and then allowed to stabilize. After a suitable period of stabilization, such as between about 5-20 minutes, the flexible shells may be dipped into an overcoat dispersion. A suitable overcoat dispersion may be made using the same material employed in the base layers. The flexible shells on the mandrels are then mounted on a rack and allowed to volatilize, such as, for example, about 15 minutes.

The entire silicone elastomer shell structure is vulcanized or cured in an oven at elevated temperatures. The temperature of the oven is preferably kept between about 200° F. and about 350° F. for a curing time preferably between about 20 minutes and about 1 hour, 40 minutes. Upon removal from the oven, the mandrel/shell assembly is placed in a solvent for the solid particles, and the solid particles allowed to dissolve. The solvent does not affect the structure or integrity of the silicone elastomer. When the solid particles have dissolved, the assembly is removed from the solvent and the solvent evaporated. The shell can then be stripped from the mandrel. At this point, it is preferable to place the shell in a solvent for the solid particles and gently agitate it to ensure complete dissolution of all the solid particles. When the shell is removed from the solvent, the solvent is evaporated.

Dissolving the solid particles leaves behind open, interconnected, cavities in the surface of the shell where the salt had been.

After finishing the shell according to the steps described above, the steps required to make a finished breast implant prosthesis may be similar to those known in the art. For example, an opening left by the dip molding process is patched with uncured sheeting, usually made of silicone rubber. Then, if the prosthesis is to be filled with silicone gel, this gel is added and cured, the filled prosthesis packaged, and the packaged prosthesis sterilized. If the prosthesis is to be inflated with a saline solution, a one-way valve is assembled and installed, the prosthesis is post cured if required, and the prosthesis is then cleaned, packaged and sterilized. A combination breast implant prosthesis can also be made wherein a gel-filled sac is positioned inside the shell to be surrounded by saline solution.

In addition to the aforementioned dipping process, the flexible shell for the prosthetic implant may be formed using a molding process. For example, a rotational molding process such as described in Schuessler, U.S. Pat. No. 6,602,452 the entire disclosure of which is incorporated herein, may be used. The process for forming texturing on the exterior surface may be done using a dipping technique after the shell is molded, but another method is to roughen the inside of the mold. For example, a mold having a generally smooth interior surface except for rough areas as described above will produce an implant shell having discrete fixation surfaces. The rotational molding process is advantageous because the entire implant shell may be formed in relatively few manufacturing steps.

Although the invention has been described and illustrated with a certain degree of particularity, it is understood that the present disclosure has been made only by way of example, and that numerous changes in the combination and arrangement of parts can be resorted to by those skilled in the art without departing from the scope of the invention, as hereinafter claimed.

What is claimed is:

1. A breast prosthesis for implantation in a human being, the prosthesis comprising:
   an implantable member comprising an elastomeric shell including an exterior surface defined by an anterior face and a posterior face; and
   a fixation region defined by a texture molded into the anterior face of the shell, the texture being different from a balance of the exterior surface of the shell, the fixation region comprising a plurality of fixation regions in a radiating configuration;
   the prosthesis being structured such that when implanted adjacent a muscle group in a human being, the fixation region can be generally aligned with an alignment of said muscle group.

2. The prosthesis of claim 1 wherein the fixation region has a first texture and said balance has a second texture different from the first texture.

3. The prosthesis of claim 1 configured for implantation in a breast of a human being and wherein the fixation region is positioned and configured to generally align with a pectoral muscle group when the prosthesis is so implanted in the breast of the human being.

4. The prosthesis of claim 1 configured for placement in a breast of a human being and wherein the fixation region is positioned to generally align with at least one of a pectoralis major muscle group and a pectoralis minor muscle group when the prosthesis is so implanted in the breast of the human being.

5. The prosthesis of claim 1 wherein the fixation region extends substantially entirely across said anterior face.

6. The prosthesis of claim 1 wherein each of the plurality of fixation regions has a substantially constant width of between about 2 mm and about 15 mm.

7. A mammary prosthesis comprising:
 a implantable member comprising a silicone elastomeric shell including an exterior surface defined by an anterior face, a posterior face and a peripheral region between the anterior face and the posterior face, said exterior surface comprising at least one generally elongated fixation region defined by a texture molded into the exterior surface of the shell which is different from a balance of the exterior surface of the shell, the fixation region extending along the peripheral region and across at least one of the posterior face and the anterior face;
 the fixation region being configured such that when the prosthesis is implanted in a breast of a human being, the fixation region generally aligns with an alignment of at least one of a pectoralis major muscle group and a pectoralis minor muscle group.

8. The prosthesis of claim 7 wherein the at least one generally elongated fixation region includes a plurality of generally elongated regions forming a substantially radiating configuration.

9. The prosthesis of claim 7 wherein the balance of the exterior surface is substantially smooth.

10. The prosthesis of claim 1 wherein the balance of the exterior surface is a relatively less textured surface than the fixation region texture.

11. The prosthesis of claim 10 wherein the balance of the exterior surface is a matte finish surface.

12. A breast prosthesis for implantation in a human being, the prosthesis comprising:
 an implantable member comprising an elastomeric shell including an exterior surface defined by an anterior face and a posterior face;
 a fixation region defined by a first texture integrally molded into the anterior face of the shell;
 a second texture integrally molded into the posterior surface of the shell, the second texture being a less textured surface than the first texture.

13. The prosthesis of claim 12 wherein the second texture is a matte finish surface.

14. A breast prosthesis for implantation in a human being, the prosthesis comprising:
 an implantable member comprising an elastomeric shell including an exterior surface defined by an anterior face and a posterior face; and
 a fixation region defined by a texture molded into the anterior face of the shell and having a substantially constant width of between about 2 mm and about 15 mm, the texture being different from a balance of the exterior surface of the shell;
 the prosthesis being structured such that when implanted adjacent a muscle group in a human being, the fixation region can be generally aligned with an alignment of said muscle group.

15. A breast prosthesis for implantation in a human being, the prosthesis comprising:
 an implantable member comprising an elastomeric shell including an exterior surface defined by an anterior face and a posterior face; and
 a fixation region defined by a texture molded into the anterior face of the shell, the texture being different from a balance of the exterior surface of the shell, and the balance of the exterior surface being a matte finish and being relatively less textured than the fixation region texture;
 the prosthesis being structured such that when implanted adjacent a muscle group in a human being, the fixation region can be generally aligned with an alignment of said muscle group.

\* \* \* \* \*

UNITED STATES PATENT AND TRADEMARK OFFICE
CERTIFICATE OF CORRECTION

PATENT NO. : 8,506,627 B2
APPLICATION NO. : 12/540317
DATED : August 13, 2013
INVENTOR(S) : Dennis Van Epps et al.

It is certified that error appears in the above-identified patent and that said Letters Patent is hereby corrected as shown below:

On the Title Page
On page 3, in column 2, under "Other Publications", line 28, delete "Hydrosels," and insert -- Hydrosols, --, therefor.

In the Specification
In column 4, line 40, delete "surface; and" and insert -- surface; --, therefor.
In column 4, line 44, delete "surfaces." and insert -- surfaces; --, therefor.
In column 4, line 48, delete "texture." and insert -- texture; and --, therefor.

In the Claims
In column 11, line 7, in claim 7, delete "a" and insert -- an --, therefor.

Signed and Sealed this
Third Day of March, 2015

Michelle K. Lee
*Deputy Director of the United States Patent and Trademark Office*